US006490075B1

(12) United States Patent
Scheps et al.

(10) Patent No.: US 6,490,075 B1
(45) Date of Patent: Dec. 3, 2002

(54) ACOUSTO-OPTIC TUNABLE FILTER HYPERSPECTRAL IMAGING SYSTEM

(75) Inventors: Richard Scheps, Rancho Santa Fe; Jon S. Schoonmaker, San Diego, both of CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/930,900

(22) Filed: Aug. 16, 2001

(51) Int. Cl.[7] .............................. G02F 1/11; G02F 1/33; G01J 3/00; H01J 3/14
(52) U.S. Cl. ..................... 359/285; 359/287; 359/305; 359/308; 359/314; 359/494; 359/573; 356/300; 250/235; 250/339.07; 348/769; 372/25
(58) Field of Search ................... 359/285, 287, 359/276, 305, 308, 314, 494, 566, 569, 573, 589, 722; 348/769, 754; 250/235, 338.5, 339.07, 339.08, 339.12; 356/300, 243.1, 326; 372/13, 25

(56) References Cited

U.S. PATENT DOCUMENTS

| 3,679,288 A | | 7/1972 | Harris | |
|---|---|---|---|---|
| 4,490,845 A | | 12/1984 | Steinbruegge et al. | |
| 4,639,092 A | | 1/1987 | Gottlieb et al. | |
| 5,410,371 A | | 4/1995 | Lambert | |
| 5,687,020 A | * | 11/1997 | Park et al. | 359/305 |
| 5,796,512 A | * | 8/1998 | Wachman et al. | 359/308 |
| 6,011,256 A | * | 1/2000 | Takada | 250/235 |
| 6,014,245 A | * | 1/2000 | Xu et al. | 359/285 |
| 6,072,813 A | * | 6/2000 | Tournois | 372/25 |
| 6,188,507 B1 | * | 2/2001 | Thomas | 359/305 |

* cited by examiner

Primary Examiner—Loha Ben
(74) Attorney, Agent, or Firm—Harvey Fendelman; Michael A. Kagan; Peter A. Lipovsky

(57) ABSTRACT

The present invention has applications that include detecting color variation in a region, for example, color variations due to temperature changes in an area of ocean water, and, in a more specific application, detecting bioluminescence of certain organisms known to attach themselves to various objects. In one aspect of the invention, an acousto-optic tunable filter hyperspectral imaging system is moved across the region to collect a series of images in which each image represents the intensity of light at a different wavelength. In one embodiment, the acousto-optic tunable filter hyperspectral imaging system includes a motion platform for positioning the acousto-optic tunable filter hyperspectral imaging system over successive Y-coordinates of a region in a direction substantially parallel to a direction of motion of the motion platform. In one such embodiment, the motion platform may be an aircraft or any other platform suitable for moving the acousto-optic tunable filter hyperspectral imaging system over the region.

35 Claims, 3 Drawing Sheets

ACOUSTO-OPTIC TUNABLE FILTER HYPERSPECTRAL IMAGING SYSTEM

BACKGROUND OF THE INVENTION

The present invention relates generally to generating an image of a region from reflected and scattered light at selected wavelengths to enhance the contrast of objects within the region. More specifically, the present invention relates to hyperspectral imaging systems.

SUMMARY OF THE INVENTION

The present invention is a technique for creating images at different wavelengths of light and also for detecting variations in the images created. It may be used, for example, to show variations that exist or occur in an image area such as temperature gradients, or to detect changes that occur in an image area such as the entry into, departure from, or presence or absence in the area of an object or matter. The image area may be a region of water, land, space or any region that contains matter or is void.

In a specific application, this invention has applications to detecting bioluminescence of certain organisms known to attach themselves to various objects. In another specific application, fluorescence spectra characteristic of toxic gases and other chemicals may be detected.

In one aspect of the invention, an acousto-optic tunable filter hyperspectral imaging system is moved across a region to collect a rapid series of images of the entire region. Each image represents the intensity of light reflected by matter in the region at a different wavelength. The acousto-optic tunable filter hyperspectral imaging system may include a platform for moving the acousto-optic tunable filter hyperspectral imaging system over successive Y-coordinates of a region in a direction substantially parallel to a direction of motion of the platform. The platform may be an aircraft or any other platform suitable establishing relative motion between the acousto-optic tunable filter hyperspectral imaging system and the region.

In another aspect of the invention, light is received from a region at successive X-coordinates. In this aspect, the acousto-optic tunable filter hyperspectral imaging system may include input optics for receiving light from the region and scanning optics for aiming the input optics at successive X-coordinates of a "slice" of the region in a direction substantially perpendicular to the direction of motion of the motion platform. Light received from the region by the input optics is collimated, and the collimated light is polarized by a linear polarizer. The collimator and the linear polarizer may be any device or combination of devices suitable for collimating and polarizing the light received from the region by the input optics. In one embodiment, the collimated and polarized light is directed to an acousto-optic tunable filter which images a portion of the light received from the region at a plurality of selected wavelengths.

In another aspect of the invention, the passband wavelengths of the acousto-optic tunable filter may be stepped in increments small enough to detect extremely small variations in color. The passband wavelengths of the acousto-optic tunable filter may then be stepped in small increments, e.g. on the order of five nanometers.

In a further aspect of the invention, the intensity of the light received from the region at a specific wavelength in a selected series of stepped wavelengths is recorded for image processing. An image recorder may be used to record the intensity of the light received from the acousto-optic tunable filter for each of the plurality of selected wavelengths.

In another aspect of the invention, the acousto-optic tunable filter hyperspectral imaging system may further include an illumination source for illuminating the region. The illumination source may be any device suitable for illuminating the entire region or a portion of the region that includes an area from which light is being received by the input optics. In one such embodiment, the illumination source may be a laser or an ultra-violet lamp.

BRIEF DESCRIPTION OF THE DRAWINGS

The above and other aspects, features and advantages of the present invention will be more apparent from the following more specific description thereof, presented in conjunction with the following drawings wherein.

Corresponding reference characters indicate corresponding elements throughout the several views of the drawings.

DESCRIPTION OF SOME EMBODIMENTS

Figure 1:
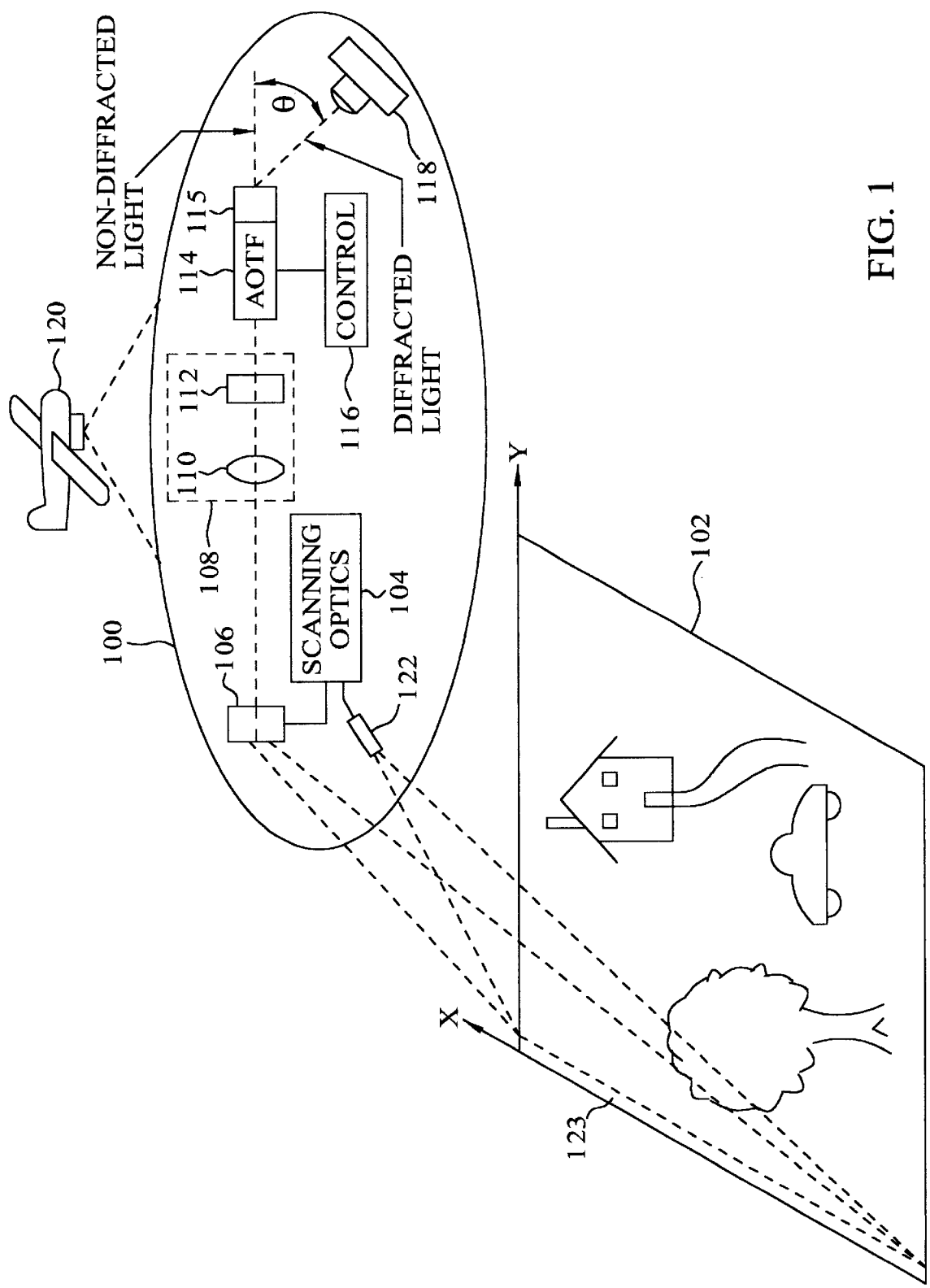
FIG. 1 is a diagram of an acousto-optic tunable filter hyperspectral imaging system on a motion platform according to an embodiment of the present invention.

In an imaging spectrometer incorporating an acousto-optical tunable filter, light having a selected wavelength received from a two-dimensional image is passed from an entry port to an exit port of the acousto-optical tunable filter. An hyperspectral imaging system records multiple images of a region, with each image depicting the region at a different wavelength of light. Typically, the wavelengths of spectrally adjacent images differ by three to five nanometers (3–5 nm).

An acousto-optical tunable filter (AOTF) is typically constructed of a birefringent material that is transparent to the wavelengths of interest, usually but not necessarily the visible spectrum. A piezo-electric transducer is attached to the birefringent material so that when an RF signal is applied to the piezo-electric transducer, a standing compression or shear wave is established in the birefringent material. The index of refraction in the birefringent material varies as a function of pressure, so that alternating regions of high and low pressure maintained in the birefringent material by the piezo-electric transducer have different indices of refraction. The alternating regions of higher and lower refractive indices form a diffraction grating in the birefringent material that disperses incident light in the same way as other types of diffraction gratings. An advantage of using an acousto-optical tunable filter over other types of diffraction gratings is that the spacing of the diffraction grating in an acousto-optical tunable filter may be changed to pass a different wavelength of light in a microsecond or less. A series of, for example, a hundred images each representing the intensity of light reflected or scattered from a region at a different wavelength may therefore be recorded within a time interval on the order of half a millisecond, depending on the birefringent material. For example, the wavelength spacing in some birefringent materials can be changed within a time interval on the order of 10 microseconds. A series of one hundred images each taken in 10 microseconds would only require an acquisition time of about 100 times 10 microseconds, i.e. about one millisecond.

The bandwidth of an acousto-optical tunable filter is also the reciprocal of the frequency resolution. The bandwidth decreases with the center frequency and with the difference between the refractive indices in the alternating regions of high and low pressure in the birefringent material. Several useful birefringent materials for high resolution acousto-optical tunable filters for applications in the ultraviolet, visible, and near infra-red wavelengths are alpha-quartz, lithium niobate, calcium molybdate, tellurium dioxide, thallium arsenic selenide, thallium phosphorus selenide, and mercurous chloride. For the visible range used in the example of FIG. 1, an acousto-optical tunable filter crystal element made of, for example, paratellurite is preferred, because it has a bandpass of 2.64 nm that provides about 100 color bands over the visible range of wavelengths from about 400 nm to about 700 nm. A typical bandwidth of an acousto-optical tunable filter available from Aurora Photonics, Inc. in Santa Clara, Calif. is one nanometer at a wavelength of 633 nm.

FIG. 1 is a diagram of an acousto-optic tunable filter hyperspectral imaging system 100 for use with a motion platform in accordance with an embodiment of the present invention. Shown in FIG. 1 are a region 102, scanning optics 104, a reflector 106, input optics 108 including a collimator 110 and a linear polarizer 112, an acousto-optic tunable filter 114, an imaging spectrometer 115, control electronics 116, an image recorder 118, a motion platform 120, and a light source 122.

The region 102 may be, for example, an area on the ground or ocean. The region 102 is viewed from a motion platform, for example, an aircraft.

In operation, the acousto-optic tunable filter (AOTF) hyperspectral imaging system 100 obtains successive one-dimensional images of the region 102. As used herein, "one-dimensional" means a very narrow section of the region, e.g. on the order of one millimeter along the Y axis. By varying the RF signal applied to the AOTF 114, the AOTF 114 generates a multitude of images of each "one-dimensional" slice of the region 102 at its output port, each image being at a different wavelength of light. By way of example, one such "one dimensional" slice 123 of region 102 is illustrated in FIG. 1. As the image of the region is scanned across the entry port of the acousto-optical tunable filter 114, multiple images at different wavelengths of light of adjacent one-dimensional slices of the image are reproduced at the exit port of the imaging spectrometer 115. The scanning of one-dimensional slices of the region 102 provides much higher resolution than would be produced by imaging an entire two-dimensional image of the region 102. The higher resolution is due to lower image distortion and higher degree of collimation of each of the one-dimensional images compared to that of a two-dimensional image. The scanning optics 104 and the reflector 106 aim incoming light from the region 102 to the input optics 108 from successive X-coordinates of the region 102 perpendicular to the line of motion of the motion platform 120. The reflector 106 may be, for example, one or more mirrors or prisms controlled by a motor according to well known techniques to reflect light from successive X-coordinates of the region 102 to the input optics 108.

The input optics 108 receive the light from the scanning optics 104 corresponding to the successive X-coordinates of each pixel in the region 102. The collimator 110 collimates the light reflected by the reflector 106. The polarizer 112 transmits only a single polarization of the collimated light from the collimator 110 in a direction perpendicular to the direction of propagation of the acoustic waves generated by the acousto-optic tunable filter 114.

The acousto-optic tunable filter 114 receives the collimated and polarized light from the input optics 108 for each scan performed by the scanning optics 104. The control electronics 116 selects the wavelength of light to be transmitted by the acousto-optic tunable filter 114. A commercial source for the acousto-optic tunable filter 114 and the control electronics 116 is Aurora Photonics Inc. in Santa Clara, Calif.

The image recorder 118 may be, for example, a conventional charge-coupled device (CCD) camera including a lens for focusing the diffracted light from the acousto-optic tunable filter 114 onto the camera's charge-coupled device array. The image recorder 118 receives the series of pixels of the image that are received from the region 102 scanned at successive X-coordinates and are diffracted by the acousto-optic tunable filter 114 and stores a value of intensity corresponding to each pixel received as a linear image in a column of the charge-coupled device array. The charge-coupled device array can hold about 100 such linear images, and each image corresponds to a separate wavelength. A new series of color-resolved linear images is scanned and recorded by the image recorder 118 for each Y-coordinate of the region 102 until the region 102 has been completely scanned in both the X-dimension and the Y-dimension, there being multiple scans, each at a different wavelength for each scan in the X-dimension. The successive Y-coordinates of the entire two-dimensional image may be reassembled using a reconstruction image processor to view a spectrally resolved version of the full-color image as it is scanned across the entry port of the acousto-optical tunable filter. Generally, the X-dimension is scanned perpendicular to the motion of the motion platform 120 and the Y-dimension is scanned in the direction of motion of the motion platform 120. This type of two-dimensional scanning is called "push-broom" scanning.

The acousto-optic tunable filter 114 operates as a wavelength-adjustable camera filter so that multiple images of a region may be recorded at different wavelengths at a faster rate and at a higher signal-to-noise ratio than previous airborne hyperspectral imaging systems. The intensity measurements for each pixel in the region 102 recorded by the image recorder 118 may be downloaded to a computer for image processing and color analysis at each selected wavelength according to well known techniques.

Figure 2:
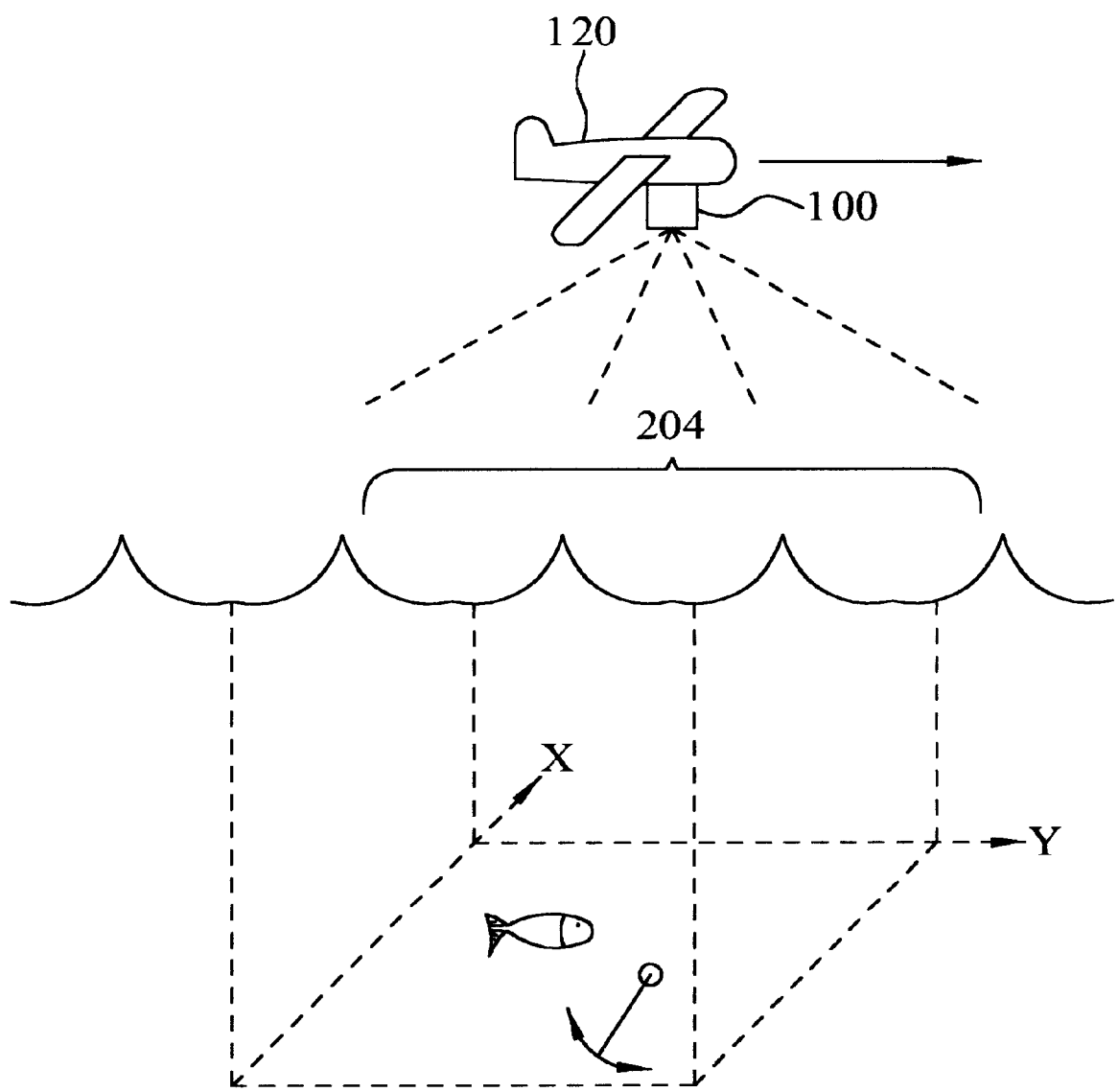
FIG. 2 is a diagram of the acousto-optic tunable filter hyperspectral imaging system of FIG. 1 illustrating its use for scanning multiple images of an area of ocean water.

FIG. 2 is a diagram of the acousto-optic tunable filter hyperspectral imaging system 100 of FIG. 1 illustrating its use for scanning multiple images of a column of ocean water. Shown in FIG. 2 are an acousto-optic tunable filter hyperspectral imaging system 100, a motion platform 120, a light source 122, and a column of ocean water 204.

The motion platform 120 may be, for example, an aircraft or a satellite. The motion of the motion platform 120 provides successive Y-coordinates for the image received from the column of ocean water 204. In practice, pitch and yaw resulting from wind currents and other factors generally prevent maintaining the motion of the motion platform 120 perfectly straight and level. Compensation for incidental deviations in the motion of the motion platform 120 may be calculated, for example, by a computer for each image recorded by the image recorder 118. To avoid loss of resolution in the compensated image due to aberrations in the input optics 108, high quality, large aperture, wide field of view optics should be used for the collimator 110 and the polarizer 112 in the acousto-optic tunable filter hyperspectral imaging system 100. A suitable aperture size for the collimator 110 and the polarizer 112 is about ten centimeters.

In operation, the motion of the motion platform 120 positions the acousto-optic tunable filter hyperspectral imaging system 100 over successive Y-coordinates of the column of ocean water 204 as the acousto-optic tunable filter hyperspectral imaging system 100 acquires multiple images at selected wavelengths, for example, at a selected wavelength spacing of 3 nm stepped sequentially or non-sequentially from 400 nm to 700 nm. The multiple images may be downloaded from the image recorder 118 to a computer and processed digitally according to well known image processing techniques, such as image subtraction, to enhance the visibility of objects in the column of ocean water 204 or on the ocean floor. Similar techniques may be used to detect temperature changes across the column of ocean water 204 by color variation using a selected wavelength spacing of five nanometers or less.

Alternatively, the acousto-optic tunable filter hyperspectral imaging system 100 may include the light source 122. The light source 122 may be, for example, a laser or an ultra-violet lamp for use at night or to record phenomena such as laser-induced fluorescence. The fluorescence spectrum of certain biological organisms that attach themselves to underwater objects is well known, therefore the acousto-optic tunable filter hyperspectral imaging system 100 can highlight areas containing objects in the column of ocean water 204 that are emitting the characteristic fluorescence while blocking out background fluorescence or bioluminescence from the same areas. For better image acquisition and higher signal to noise ratio, the light source 122 may be scanned in parallel with the scanning optics 104 to illuminate successive X-coordinates across the column of ocean water 204 pixel by pixel. On the other hand, the large aperture of the acousto-optic tunable filter hyperspectral imaging system 100 may also be used advantageously to detect stimulated bioluminescence in close proximity to underwater objects.

Other advantages of the acousto-optic tunable filter hyperspectral imaging system 100 are its small size and solid state construction, which may be implemented in a device as a guidance system to lead the device to an underwater object by detecting the bioluminescent signal emitted from the underwater object by biological organisms attached to the underwater object.

Figure 3:
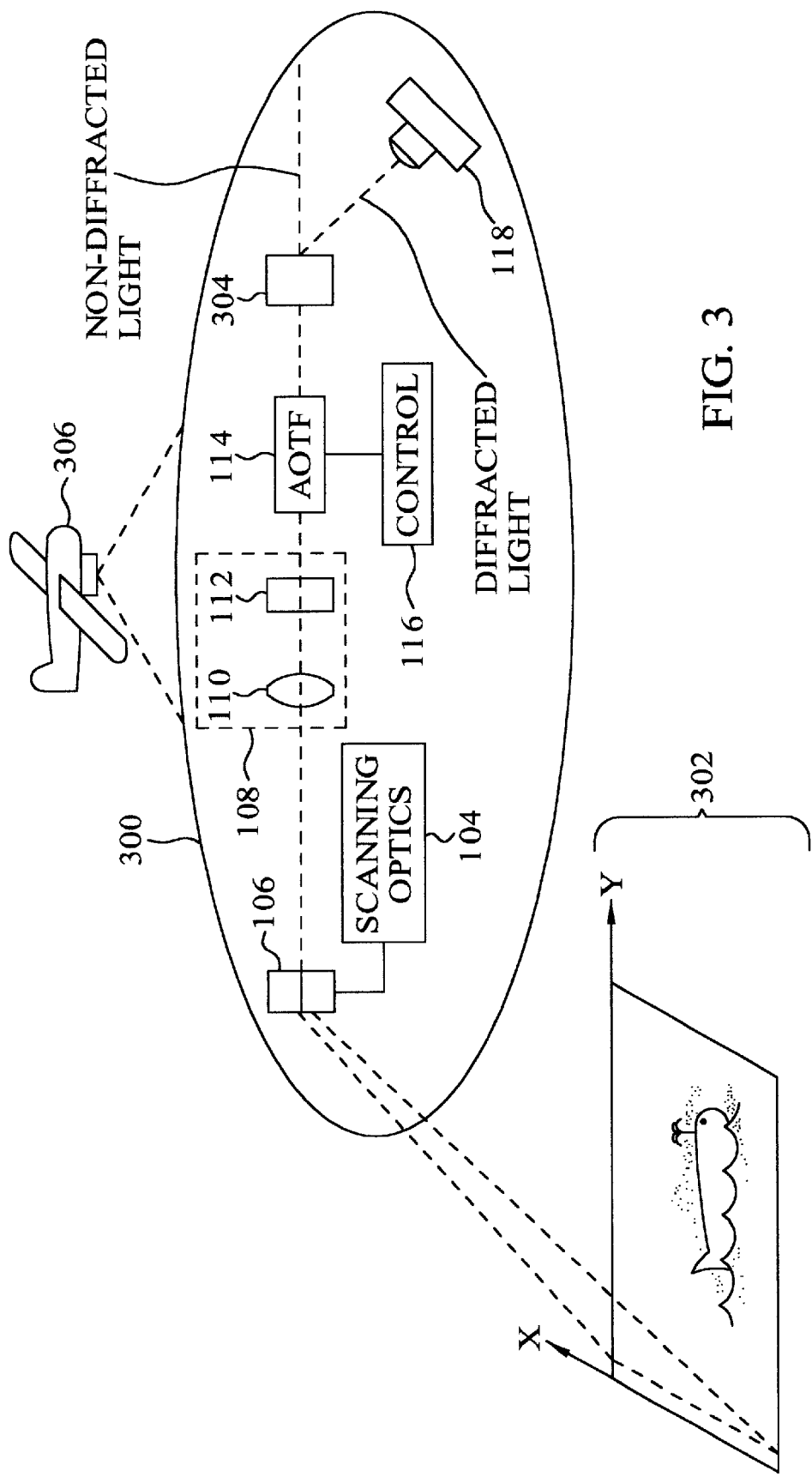
FIG. 3 is a diagram of an acousto-optic tunable filter hyperspectral imaging system on a motion platform according to another embodiment of the present invention.

FIG. 3 is a diagram of an acousto-optic tunable filter hyperspectral imaging system 300 according to an alternative embodiment of the present invention. Shown in FIG. 3 are scanning optics 104, a reflector 106, input optics 108 including a collimator 110 and a linear polarizer 112, an acousto-optic tunable filter 114, control electronics 116, an image recorder 118, a region 302, a polarization separator 304, and a motion platform 306.

In the acousto-optic tunable filter hyperspectral imaging system 300, there is no imaging spectrometer as in the embodiment illustrated in FIG. 1. The motion platform 306 includes the examples described with reference to FIG. 1, and if only a single scene is to be imaged, the motion platform 306 may be any platform suitable for maintaining a fixed position relative to the scene 302. The acousto-optic tunable filter hyperspectral imaging system 300 also differs from the embodiment illustrated in FIG. 1 in that the linear polarizer 112 polarizes the collimated light from the collimator 110 in a direction parallel rather than perpendicular to the direction of propagation of the acoustic waves generated by the acousto-optic tunable filter 114. In this example, both diffracted light and non-diffracted light from the acousto-optic tunable filter 114 propagate collinearly, but the polarization of the diffracted light is rotated by the acousto-optic tunable filter 114. The polarization separator 304 splits the diffracted light having the rotated axis of polarization from the non-diffracted light having the non-rotated axis of polarization. The polarization separator 304 may be, for example, a Glan-Taylor prism.

In operation, the acousto-optic tunable filter (AOTF) hyperspectral imaging system 300 obtains successive two-dimensional images of the region 302. As used herein, "two-dimensional" means the entire area of the region defined between the X-axis and the Y axis. By varying the RF signal applied to the AOTF 114, the AOTF 114 generates a multitude of images of the region 302 at its output port, each image being at a different wavelength of light.

The image recorder 118 may be, for example, a conventional charge-coupled device (CCD) camera including a lens for focusing the diffracted light from the acousto-optic tunable filter 114 onto the camera's charge-coupled device array. The image recorder 118 receives the series of pixels of each "two-dimensional" image received from the region 302 diffracted by the acousto-optic tunable filter 114 and stores a value of intensity corresponding to each pixel received as a "two-dimensional" image in the charge-coupled device array. A new series of color-resolved pixels is recorded by the image recorder 118 for each "two-dimensional" image of the region 302.

The acousto-optic tunable filter 114 operates as a wavelength-adjustable camera filter so that multiple images of a region may be recorded at different wavelengths at a faster rate and at a higher signal-tonoise ratio than previous airborne hyperspectral imaging systems. The intensity measurements for each pixel in the region 102 recorded by the image recorder 118 may be downloaded to a computer for image processing and color analysis at each selected wavelength according to well known techniques.

The acousto-optic tunable filter hyperspectral imaging systems described above may also be used to search for toxic gases and drug-related ether emissions in soil, air, or water. Each of these toxic gases, including benzene, gasoline, nerve gas, etc., has a characteristic fluorescence spectrum that may readily be identified by illuminating the region 302 with a laser or an ultraviolet lamp and recording the fluorescence spectrum with an acousto-optic tunable filter hyperspectral imaging system such as described above.

While the invention herein disclosed has been described by means of specific embodiments and applications thereof, other modifications, variations, and arrangements of the present invention may be made in accordance with the above teachings other than as specifically described to practice the invention within the spirit and scope defined by the following claims.

What is claimed is:

1. An acousto-optic tunable filter hyperspectral imaging system comprising:
    a motion platform for positioning the acousto-optic tunable filter hyperspectral imaging system over a region;
    an acousto-optic tunable filter coupled to the motion platform for diffracting a portion of light received from the region at each of a plurality of selected wavelengths; and
    an image recorder coupled to the acousto-optic tunable filter for recording an intensity of diffracted light from the region for each of the plurality of selected wavelengths.

2. The acousto-optic tunable filter hyperspectral imaging system of claim 1 further comprising an imaging spectrometer coupled to the acousto-optic tunable filter.

3. The acousto-optic tunable filter hyperspectral imaging system of claim 1 further comprising:

input optics coupled to the motion platform for receiving light from the region;

scanning optics coupled to the input optics for aiming the input optics at successive X-coordinates of the region in a direction substantially perpendicular to the direction of motion of the motion platform;

a collimator coupled to the input optics for collimating light received from the region; and a linear polarizer coupled to the collimator to polarize collimated light.

4. The acousto-optic tunable filter hyperspectral imaging system of claim 1 wherein the image recorder comprises a charge-coupled device camera.

5. The acousto-optic tunable filter hyperspectral imaging system of claim 1 wherein the motion platform is an aircraft.

6. The acousto-optic tunable filter hyperspectral imaging system of claim 1 wherein the image recorder comprises an image processor for reassembling two-dimensional images from one-dimensional scans of successive X-coordinates for successive Y-coordinates of the region.

7. The acousto-optic tunable filter hyperspectral imaging system of claim 1 wherein the plurality of selected wavelengths has a range from about 400 nm to about 700 nm.

8. The acousto-optic tunable filter hyperspectral imaging system of claim 1 wherein the plurality of selected wavelengths has a spacing of no more than five nanometers.

9. The acousto-optic tunable filter hyperspectral imaging system of claim 1 wherein the region comprises an area of water having a color that varies with temperature.

10. The acousto-optic tunable filter hyperspectral imaging system of claim 1 further comprising an illumination source coupled to the motion platform for illuminating the region.

11. The acousto-optic tunable filter hyperspectral imaging system of claim 10 wherein the illumination source is a laser or an ultraviolet lamp.

12. The acousto-optic tunable filter hyperspectral imaging system of claim 1 wherein light diffracted by the acousto-optic tunable filter propagates collinearly with non-diffracted light.

13. The acousto-optic tunable filter hyperspectral imaging system of claim 12 wherein light diffracted by the acousto-optic tunable filter has an axis of polarization that is rotated with respect to that of non-diffracted light.

14. The acousto-optic tunable filter hyperspectral imaging system of claim 13 further comprising a polarization separator coupled to the acousto-optic tunable filter for directing diffracted light to the image recorder.

15. The acousto-optic tunable filter hyperspectral imaging system of claim 14 wherein the region includes stimulated bioluminescence.

16. An acousto-optic tunable filter hyperspectral imaging system comprising:

a motion platform;

an acousto-optic tunable filter coupled to the motion platform for diffracting a portion of light from a region for a series of selected wavelengths;

an image recorder coupled to the acousto-optic tunable filter for recording the intensity of diffracted light for each of the series of selected wavelengths; and an illumination source for illuminating the region.

17. The acousto-optic tunable filter hyperspectral imaging system of claim 16 further comprising:

input optics coupled to the motion platform for receiving light from the region;

scanning optics coupled to the input optics for aiming the input optics at successive X-coordinates of the region perpendicular to a direction of motion of the motion platform;

a collimator coupled to the input optics for collimating the light received from the region; and a linear polarizer coupled to the collimator to polarize collimated light.

18. The acousto-optic tunable filter hyperspectral imaging system of claim 16 wherein the illumination source comprises a laser.

19. The acousto-optic tunable filter hyperspectral imaging system of claim 16 wherein the illumination source is scanned in parallel with the scanning optics.

20. The acousto-optic tunable filter hyperspectral imaging system of claim 16 wherein the illumination source comprises an ultraviolet lamp.

21. The acousto-optic tunable filter hyperspectral imaging system of claim 20 wherein the illumination source stimulates a characteristic fluorescence spectrum from a location within the region.

22. The acousto-optic tunable filter hyperspectral imaging system of claim 21 wherein the characteristic fluorescence spectrum is representative of a biological organism.

23. The acousto-optic tunable filter hyperspectral imaging system of claim 21 wherein the characteristic fluorescence spectrum is representative of a toxic gas.

24. An acousto-optic tunable filter hyperspectral imaging system comprising:

means for positioning an acousto-optic tunable filter over successive Y-coordinates of a region in a direction substantially parallel to a direction of motion;

means for receiving light from the region at each of the successive Y-coordinates;

means for diffracting a portion of light received from the region at each of a stepped series of wavelengths; and means for recording an intensity of diffracted light at each of the selected wavelengths.

25. The acousto-optic tunable filter hyperspectral imaging system of claim 24 further comprising:

means for aiming the means for receiving light from the region at successive X-coordinates of the region in a direction substantially perpendicular to the direction of motion;

means for collimating the light received from the region to produce collimated light; and means for polarizing the collimated light.

26. The acousto-optic tunable filter hyperspectral imaging system of claim 24 wherein the means for recording comprises a charge-coupled device camera.

27. The acousto-optic tunable filter hyperspectral imaging system of claim 24 wherein the means for positioning comprises an aircraft.

28. The acousto-optic tunable filter hyperspectral imaging system of claim 24 wherein the means for recording comprises an image processor for reassembling two-dimensional images from one-dimensional scans of successive X-coordinates for successive Y-coordinates of the region.

29. The acousto-optic tunable filter hyperspectral imaging system of claim 24 wherein the stepped series of wavelengths has a range from about 400 nm to about 700 nm.

30. The acousto-optic tunable filter hyperspectral imaging system of claim 24 wherein the stepped series of wavelengths has a spacing of no more than five nanometers.

31. The acousto-optic tunable filter hyperspectral imaging system of claim 24 wherein the region comprises an area of water having a color that varies with temperature.

32. The acousto-optic tunable filter hyperspectral imaging system of claim 24 further comprising means for illuminating the region.

33. The acousto-optic tunable filter hyperspectral imaging system of claim 32 wherein the means for illuminating comprises a laser or an ultraviolet lamp.

34. The acousto-optic tunable filter hyperspectral imaging system of claim 24 wherein light diffracted by the means for diffracting propagates collinearly with non-diffracted light.

35. The acousto-optic tunable filter hyperspectral imaging system of claim 34 wherein light diffracted by the means for diffracting has an axis of polarization that is rotated with respect to that of non-diffracted light.

* * * * *